(12) United States Patent
Kim et al.

(10) Patent No.: US 12,048,731 B2
(45) Date of Patent: Jul. 30, 2024

(54) APPETITE SUPPRESSION WITH PHARMACEUTICAL COMPOSITIONS CONTAINING BIGLYCAN AS AN ACTIVE INGREDIENT

(71) Applicants: KOREA UNIVERSITY RESEARCH AND BUSINESS FOUNDATION, Seoul (KR); DAEGU GYEONGBUK INSTITUTE OF SCIENCE AND TECHNOLOGY, Daegu (KR)

(72) Inventors: Hyeon Soo Kim, Seoul (KR); Eun-Kyoung Kim, Daegu (KR); Seolsong Kim, Gyeongsangnam-do (KR); Min-Jeong Shin, Seoul (KR)

(73) Assignees: DAEGU GYEONGBUK INSTITUTE OF SCIENCE AND TECHNOLOGY, Daegu (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 193 days.

(21) Appl. No.: 17/602,750

(22) PCT Filed: Apr. 10, 2020

(86) PCT No.: PCT/KR2020/004915
§ 371 (c)(1),
(2) Date: Oct. 9, 2021

(87) PCT Pub. No.: WO2020/209674
PCT Pub. Date: Oct. 15, 2020

(65) Prior Publication Data
US 2022/0160821 A1    May 26, 2022

(30) Foreign Application Priority Data
Apr. 11, 2019   (KR) .................. 10-2019-0042619

(51) Int. Cl.
| A61K 38/16 | (2006.01) |
| A61P 3/04 | (2006.01) |
| A23L 33/17 | (2016.01) |

(52) U.S. Cl.
CPC ............. *A61K 38/16* (2013.01); *A61P 3/04* (2018.01); *A23L 33/17* (2016.08)

(58) Field of Classification Search
CPC ............ A61K 38/16; A61P 3/04; A23L 33/17
See application file for complete search history.

(56) References Cited

U.S. PATENT DOCUMENTS

| 10,117,839 B2 * | 11/2018 | Harel ................. A23L 29/25 |
| 2004/0063627 A1 * | 4/2004 | Fallon .................. A61P 21/00 514/17.7 |
| 2008/0015265 A1 | 1/2008 | Rubin et al. |

FOREIGN PATENT DOCUMENTS

| EP | 0616536 B1 * | 10/1993 |
| EP | 0616536 B1 | 3/1999 |
| KR | 1020190089751 A | 7/2019 |

OTHER PUBLICATIONS

Ward, M., et al., "Regulation of pre-adipocyte proliferation and apoptosis by the small leucine-rich proteoglycans, biglycan and decorin", Cell Proliferation, 2011, pp. 343-351, vol. 44, Publisher: Blackwell Publishing Ltd., on IDS filed Oct. 9, 2021. (Year: 2011).*

(Continued)

*Primary Examiner* — Kevin S Orwig
*Assistant Examiner* — John Michael Cronin
(74) *Attorney, Agent, or Firm* — HULTQUIST, PLLC; Steven J. Hultquist

(57) ABSTRACT

The present invention relates to a pharmaceutical composition which is for preventing or treating obesity, and comprises a biglycan as an active ingredient. Biglycan according to the present invention suppresses appetite by decreasing the expression of Agrp and NPY, which are appetite pro- (Continued)

moting peptides, and increasing the expression of POMC, which is an appetite suppressing peptide, and thus is very useful as a medicine for treating obesity.

2 Claims, 2 Drawing Sheets

Specification includes a Sequence Listing.

(56) References Cited

OTHER PUBLICATIONS

Fisher, L.W., et al., "GenBank accession No. AAA52287.1, biglycan [*Homo sapiens*]", NCBI, 2016, on IDS (Year: 2016).*

Hirose, S., et al., "Attenuation of Obesity-induced Inflammation of Mice Orally Administered with Salmon Cartilage Proteoglycan , a Prophylactic Agent", Biochemical and Biophysical Research Communications, 2017, pp. 480-485, vol. 484, on IDS filed Oct. 9, 2021 (Year: 2017).*

Weber et al., Obesity and Endocrine Management of the Patient With Duchenne Muscular Dystrophy, Pediatrics; 142(Suppl 2): S43-S52. doi:10.1542/peds.2018-0333F. (Year: 2018).*

Fisher, L.W., et al., "GenBank accession No. AAA52287.1, biglycan [*Homo sapiens*]", NCBI, 2016.

Hirose, S., et al., "Attenuation of Obesity-induced Inflammation of Mice Orally Administered with Salmon Cartilage Proteoglycan, a Prophylactic Agent", Biochemical and Biophysical Research Communications, 2017, pp. 480-485, vol. 484.

Luo, N., et al., "Neuropeptide Y and Agouti-Related Peptide Mediate Complementary Functions of Hyperphagia and Reduced Energy Expenditure in Leptin Receptor Deficiency", Endocrinology, 2011, pp. 883-889, vol. 152, No. 3, Publisher: Endocrine Society.

Ward, M., et al., "Regulation of pre-adipocyte proliferation and apoptosis by the small leucine-rich proteoglycans, biglycan and decorin", Cell Proliferation, 2011, pp. 343-351, vol. 44, Publisher: Blackwell Publishing Ltd.

Cai, F., et al., "Glucose regulates AMP-activated protein kinase activity and gene expression in clonal, hypothalmic neurons expressing proopiomelanocortin: additive effects of leptin or insulin", Journal of Endocrinology, 2007, pp. 605-614, vol. 192, Publisher: Society for Endocrinology.

Cakir, I., et al., "Obesity Induces Hypothalamic Endoplasmic Reticulum Stress and Impairs Proopiomelanocortin (POMC) Post-translational Processing", The Journal of Biological Chemistry, 2013, pp. 17675-17688, vol. 288, Publisher: The American Society of Biochemistry and Molecular Biology, Inc.

Fisher, L.W., et al., "Deduced Protein Sequence of Bone Small Proteoglycan I (Biglycan) Shows Homology with Proteoglycan II (Decorin) and Several Nonconnective Tissue Proteins in a Variety of Species", The Journal of Biological Chemistry, 1989, pp. 4571-4576, vol. 264, No. 8.

Heal, D.J., et al., "What is the prognosis for new centrally-acting anti-obesity drugs?", Neuropharmacology, 2012, pp. 132-146, vol. 63, Publisher: Elsevier.

Heal, DJ, et al., "A review of late-stage CNS drug candidates for the treatment of obesity", International Journal of Obesity, 2013, pp. 107-117, vol. 37, Publisher: Macmillan Publishers Limited.

Imperatore, R., et al., "Formation of OX-1R/CB1R heteromeric complexes in embryonic mouse hypothalmic cells: Effect on intracellular calcium, 2-arachidonoyl-glcerol biosynthesis and ERK phosphorylation", Pharmcological Research, 2016, pp. 600-609, vol. 111, Publisher: Elsevier.

Mantzoros, C.S., et al., "Editorial: Leptin as a Therapeutic Agent—Trials and Tribulations", The Journal of Clinical Endocrinology & Metabolism, 2000, pp. 4000-4003, vol. 85, No. 11, Publisher: The Endocrine Society.

Oh, T.S., et al., "Hypothalamic AMPK-induced autophagy increases food intake by regulating NPY and POMC expression", Autophagy, 2016, pp. 2009-2025, vol. 12, Publisher: Taylor & Francis.

Pedersen, B.K., et al., "Role of myokines in exercise and metabolism", J. Appl. Physiol., 2007, pp. 1093-1098, vol. 103, Publisher: The American Physiological Society.

Sasaki, T., et al., "Induction of Hypothalmic Sirt1 Leads to Cessation of Feeding via Agouti-Related Peptide", Endocrinology, 2010, pp. 2556-2566, vol. 151, No. 6, Publisher: endo.endojournals.org.

\* cited by examiner

[Figure 1]
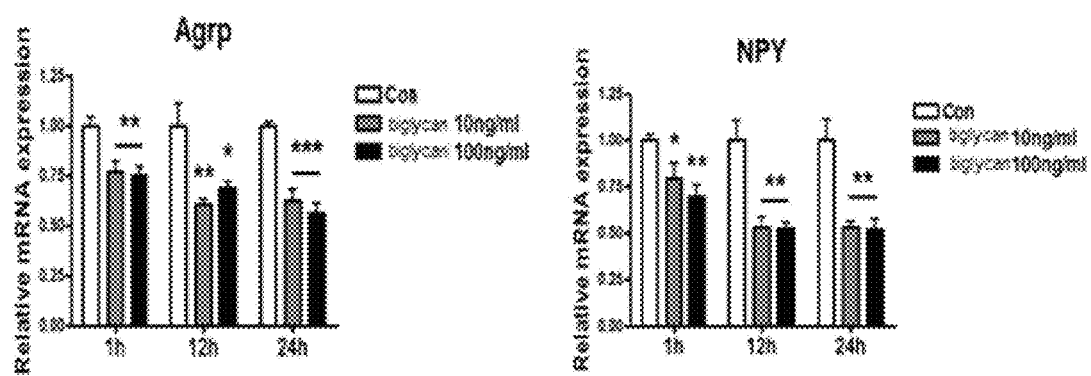
[Figure 2]
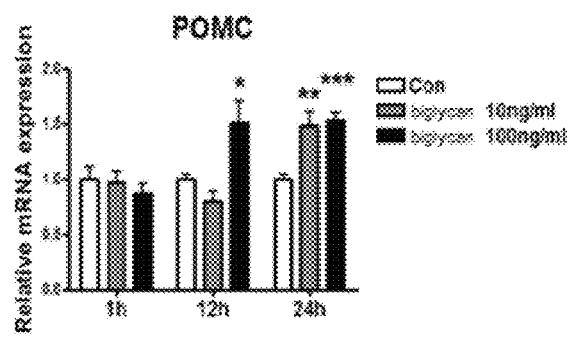

[Figure 3]
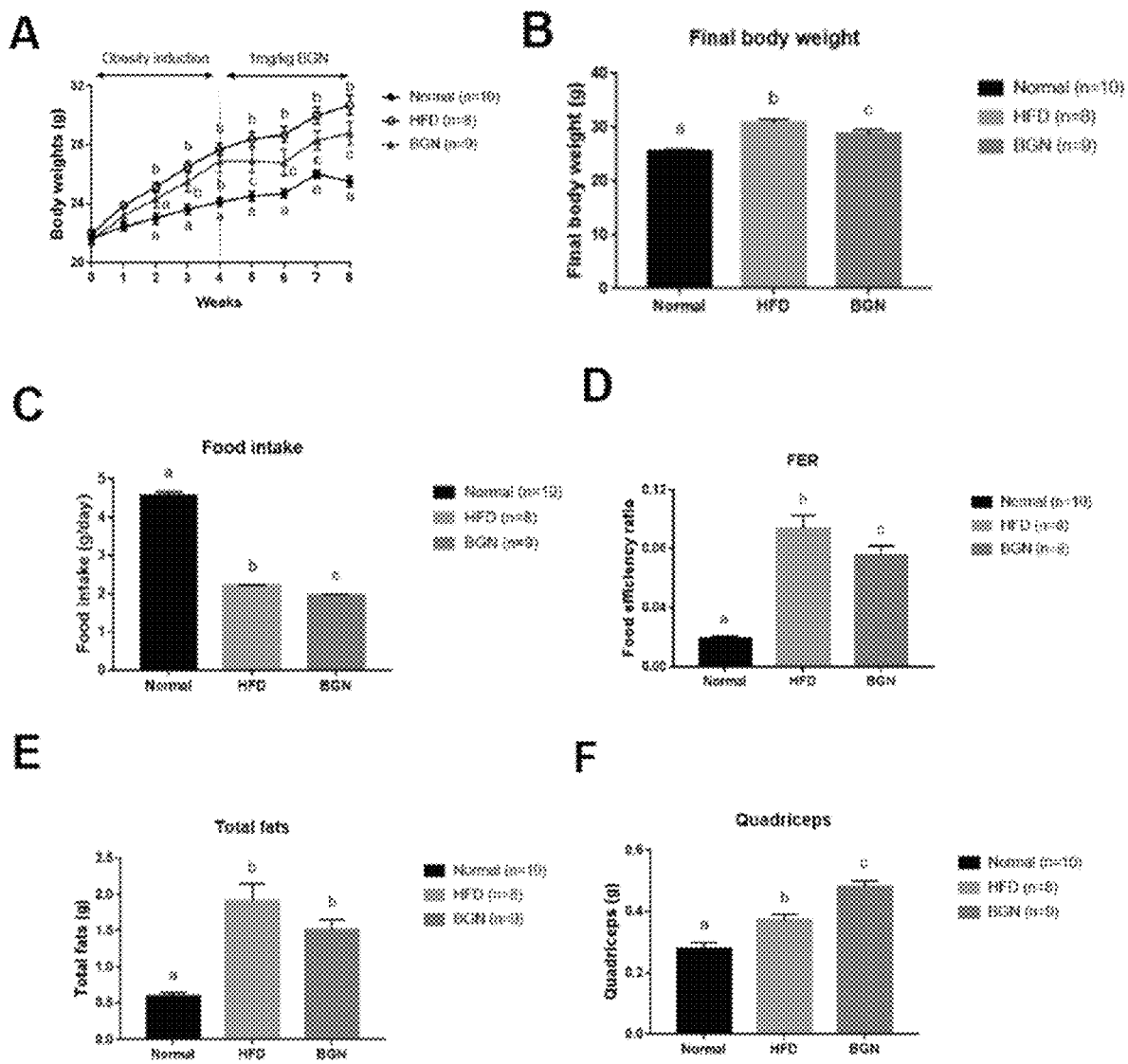

SEQUENCE LISTING

```
<160> NUMBER OF SEQ ID NOS: 1

<210> SEQ ID NO 1
<211> LENGTH: 394
<212> TYPE: PRT
<213> ORGANISM: Artificial Sequence
<220> FEATURE:
<223> OTHER INFORMATION: biglycan

<400> SEQUENCE: 1

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Glu Phe Met Leu Val Val Gly Val Gly Pro Leu Gly Leu Lys Phe
                85                  90                  95

Met Leu Val Met Gly Val Gly Pro Leu Gly Leu Lys Ser Val Pro Lys
            100                 105                 110

Glu Ile Ser Pro Asp Thr Thr Leu Leu Asp Leu Gln Asn Asn Asp Ile
        115                 120                 125

Ser Glu Leu Arg Lys Asp Asp Phe Lys Gly Leu Gln His Leu Tyr Ala
    130                 135                 140

Leu Val Leu Val Asn Asn Lys Ile Ser Lys Ile His Glu Lys Ala Phe
145                 150                 155                 160

Ser Pro Leu Arg Asn Val Gln Lys Leu Tyr Ile Ser Lys Asn His Leu
                165                 170                 175

Val Glu Ile Pro Pro Asn Leu Pro Ser Ser Leu Val Glu Leu Arg Ile
            180                 185                 190

His Asp Asn Arg Ile Arg Lys Val Pro Lys Gly Val Phe Ser Gly Leu
        195                 200                 205
```

-continued

```
Arg Asn Met Asn Cys Ile Glu Met Gly Gly Asn Pro Leu Glu Asn Ser
    210                 215                 220

Gly Phe Glu Pro Gly Ala Phe Asp Gly Leu Lys Leu Asn Tyr Leu Arg
225             230                 235                 240

Ile Ser Glu Ala Lys Leu Thr Gly Ile Pro Lys Asp Leu Pro Glu Thr
                245                 250                 255

Leu Asn Glu Leu His Leu Asp His Asn Lys Ile Gln Ala Ile Glu Leu
                260                 265                 270

Glu Asp Leu Leu Arg Tyr Ser Lys Leu Tyr Arg Leu Gly Leu Gly His
        275                 280                 285

Asn Gln Ile Arg Met Ile Glu Asn Gly Ser Leu Ser Phe Leu Pro Thr
    290                 295                 300

Leu Arg Glu Leu His Leu Asp Asn Asn Lys Leu Ala Arg Val Pro Ser
305                 310                 315                 320

Gly Leu Pro Asp Leu Lys Leu Leu Gln Val Val Tyr Leu His Ser Asn
                325                 330                 335

Asn Ile Thr Lys Val Gly Val Asn Asp Phe Cys Pro Met Gly Phe Gly
            340                 345                 350

Val Lys Arg Ala Tyr Tyr Asn Gly Ile Ser Leu Phe Asn Asn Pro Val
        355                 360                 365

Pro Tyr Trp Glu Val Gln Pro Ala Thr Phe Arg Cys Val Thr Asp Arg
    370                 375                 380

Leu Ala Ile Gln Phe Gly Asn Tyr Lys Lys
385                 390
```

APPETITE SUPPRESSION WITH PHARMACEUTICAL COMPOSITIONS CONTAINING BIGLYCAN AS AN ACTIVE INGREDIENT

CROSS-REFERENCE TO RELATED APPLICATIONS

This is a U.S. national phase under 35 USC § 371 of International Patent Application No. PCT/KR2020/004915 filed Apr. 10, 2020, which in turn claims priority under 35 USC § 119 of Korean Patent Application No. 10-2019-0042619 filed Apr. 11, 2019. The disclosures of all such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "588_SeqListing_ST25.txt" created on Oct. 9, 2021 and is 3,904 bytes in size. The sequence listing contained in this .txt file is part of the specification and is hereby incorporated by reference herein in its entirety.

TECHNICAL FIELD

The present invention relates to a pharmaceutical composition for preventing or treating obesity containing biglycan, and more specifically, to the use of biglycan, which is capable of suppressing appetite by inhibiting the expression of appetite-promoting peptides or promoting the expression of appetite-suppressing peptides, for the prevention or treatment of obesity.

BACKGROUND ART

Obesity is caused by accumulation of excessive energy due to imbalanced regulation between energy intake and expenditure, and is considered to be a disease that is more than simply a risk factor for metabolic disorders or diseases in light of the fact that obesity leads to serious diseases, comprising cardiovascular diseases such as hyperlipidemia, diabetes, arteriosclerosis, and high blood pressure (Mantzoros et al., *J. Clin. Endocrinol. Metab.*, 85:4000-2, 2000).

Efforts to treat obesity are ongoing, and obesity medications and surgical procedures such as liposuction, in addition to exercise therapy and dieting, have emerged. There are two main types of current obesity medications: one is a drug that inhibits the absorption of fat or increases the consumption of energy from ingested food, and the other is an appetite suppressant that acts on the central nervous system to suppress the appetite.

The central nervous system (CNS), particularly the hypothalamus, plays a key role in maintaining systemic energy homeostasis by integrating nutritional signals from the peripheral organs to regulate feeding and energy consumption. The arcuate nucleus of the hypothalamus (ARC) consists of two distinct neuronal populations that control energy consumption and body weight as well as food intake. Neurons expressing appetite-suppressing peptides pro-opiomelanocortin (POMC) and cocaine and amphetamine regulated transcript (CART) inhibit food intake and increase energy consumption, while neurons expressing the appetite-stimulating peptides agouti-related protein (AgRP) and neuropeptide Y (NPY) promote food intake. Recent remarkable research on obesity drugs has brought about the development of appetite suppressants acting on the central nervous system as novel drugs for treating obesity (*International Journal of Obesity* 37:107-117, 2013; *Neuropharmacology* 63:132-146, 2012). As representative examples, in 2012, the US FDA approved two new appetite suppressants, Belviq (lorcaserin) and Qsymia (containing phentermine and topiramate). In addition, exenatide (Byetta) and liraglutide (Victoza), which are GLP-1 (glucagon-like peptide), are currently approved and marketed as therapeutic agents for type 2 diabetes, and have the effect of suppressing the appetite by increasing satiety. As generally evaluated by Korean medical workers, Belviq is a drug that can be used without concern about side effects, but disadvantageously cannot be expected to realize a remarkable weight loss effect and is expensive, whereas Qsymia has a weight loss effect superior to that of Belviq, but has not been introduced into Korea and has not been approved for use in Europe due to the high incidence of complications affecting the cardiovascular system and brain, and is not recommended for cardiovascular disease patients. As such, there is still a lack of adequate appetite suppressants for the treatment of obesity.

Meanwhile, biglycan is a small proteoglycan having a hybrid chain of chondroitin sulfate and dermatan sulfate, and its function is not well known. Biglycan has 12 repeating units, each including a structure containing 24 amino acids rich in leucine, and similar proteoglycans thereto include decorin (PG-II) and fibromodulin, which have distinct differences in tissue distribution and binding capacity with collagen fibers. Proteoglycans are highly glycosylated proteins and the term generally refers to a group of molecules in which glycosaminoglycan side chains are covalently bound to proteins. Proteoglycans are found in connective tissue and are responsible for various cellular physiological functions (Fisher L. W. et al., *J. Biol. Chem.* 264:4571-4576, 1989).

In addition, biglycan is a novel myokine protein, and myokine is an active substance that is expressed, synthesized, or secreted from skeletal muscle by physical activity, that is, exercise (Pedersen et al., *Journal of Applied Physiology*, 103: 1093-98, 2007). IL-6 is a representative well-known myokine, and the myokine enhances immunity and prevents arteriosclerosis or the like. Therefore, it can be seen that the effect of preventing diabetes by exercise is due to the secretion of myokines such as biglycan, and the present inventors identified the prophylactic and therapeutic effects of biglycan on diabetes in previous studies (KR 10-2018-0007619; KR 10-2019-0007425).

However, the appetite suppression or weight loss effect of biglycan has not been elucidated, and the efficacy of biglycan on obesity is not known at all.

Accordingly, as a result of attempts to develop a drug that can treat obesity through appetite suppression by acting on the appetite-regulating central system and is harmless to the human body, the present inventors found that biglycan can inhibit the expression of appetite-promoting peptides and promote the expression of appetite-suppressing peptides, and thus can be used for the prevention or treatment of obesity, thus completing the present invention.

DISCLOSURE

Technical Problem

Therefore, it is one object of the present invention to provide a pharmaceutical composition and a food for preventing or treating obesity comprising, as an active ingredient, biglycan that acts on the appetite-regulating central system and has an appetite-suppressing effect.

It is another object of the present invention to provide a method of treating or preventing obesity comprising administering biglycan to a subject.

It is another object of the present invention to provide a use of biglycan for the treatment or prevention of obesity.

It is another object of the present invention to provide a use of biglycan for the preparation of a medicine for treating or preventing obesity.

Technical Solution

In accordance with one aspect of the present invention, the above and other objects can be accomplished by the provision of a pharmaceutical composition for preventing or treating obesity containing biglycan as an active ingredient.

In accordance with another aspect of the present invention, provided is a functional food for preventing or alleviating obesity containing biglycan as an active ingredient.

In accordance with another aspect of the present invention, provided is a method for preventing or treating obesity comprising administering biglycan to a subject.

In accordance with another aspect of the present invention, provided is the use of biglycan for the prevention or treatment of obesity.

In accordance with another aspect of the present invention, provided is the use of biglycan for the preparation of a medicine for treating or preventing obesity.

DESCRIPTION OF DRAWINGS

FIG. 1 illustrates the inhibition of mRNA expression of the appetite-stimulating peptides Agrp and NPY when treating an Agrp/NPY-expressing hypothalamic cell line with biglycan.

FIG. 2 illustrates an increase in mRNA expression of POMC, an appetite-suppressing peptide, when treating a POMC-expressing hypothalamic cell line with biglycan.

FIG. 3 illustrates the effects of biglycan on reduction in food intake and inhibition of weight gain in an obese animal model induced by a high-fat diet.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In the present invention, when treating the hypothalamic cell line with biglycan, inhibition of expression of the appetite-promoting peptide and promotion of expression of the appetite-suppressing peptide were observed, so the effect of biglycan on treating obesity was identified.

The arcuate nucleus of the hypothalamus (ARC) includes two distinct neural regions involved in the regulation of feeding behavior, including neurons expressing orexigenic neuropeptides, agouti-related protein (AgRP) and neuropeptide Y (NPY) and neurons expressing anorexigenic neuropeptides, pro-opiomelanocortin (POMC) and cocaine and amphetamine regulated transcript (CART). Accordingly, in order to determine the effect of biglycan on the feeding center in vitro, mRNA expression of AgRP and NPY as appetite-promoting peptides and POMC as an appetite-suppressing peptide was measured after treatment of cells with biglycan.

Therefore, in one aspect, the present invention is directed to a pharmaceutical composition for preventing or treating obesity containing biglycan as an active ingredient.

In the present invention, the biglycan may be represented by the amino acid sequence of SEQ ID NO: 1.

As used herein, the term "obesity" refers to a condition or disease characterized by excess body fat due to energy imbalance. Obesity can be prevented or treated through body weight loss by administering the pharmaceutical composition according to the present invention to a subject.

As used herein, the term "prevention" refers to any action that can suppress or delay the onset of obesity by administration of the pharmaceutical composition according to the present invention.

As used herein, the term "treatment" refers to any action that can ameliorate or beneficially alter the symptoms of obesity by administration of the pharmaceutical composition according to the present invention.

The obesity treatment can be applied to any mammal in which obesity may occur, and examples thereof comprise, but are not limited to, livestock such as cattle, pigs, sheep, horses, dogs and cats, as well as humans and primates, and the mammal preferably is a human.

As used herein, the term "administration" refers to an action of introducing a predetermined substance into a subject by any appropriate method, and the route of administration of the composition may be any general route, so long as it enables the drug to be delivered to target tissue. The route of administration may comprise, but is not limited to, intraperitoneal administration, intravenous administration, intramuscular administration, subcutaneous administration, intradermal administration, oral administration, topical administration, intranasal administration, intrapulmonary administration, rectal administration and the like.

As used herein, the term "appetite suppression" refers to any action that suppresses appetite or delays the onset thereof by suppressing the secretion and expression of a diet-related peptide, for example, an appetite-stimulating peptide, or promoting the secretion and expression of an appetite-suppressing peptide through administration of biglycan.

In the present invention, the biglycan preferably suppresses the expression of the appetite-stimulating peptide, and the appetite-stimulating peptide is preferably agouti-related protein (AgRP) or neuropeptide Y (NPY), but is not limited thereto.

In the present invention, the biglycan preferably enhances the expression of the appetite-suppressing peptide, and the appetite-suppressing peptide is preferably proopiomelanocortin (POMC), but is not limited thereto.

In addition, the biglycan preferably reduces food intake, and more preferably reduces food intake by suppressing appetite.

In a specific embodiment of the present invention, biglycan suppresses expression of mRNA of the appetite-promoting peptides AgRP and NPY, and enhances expression of mRNA of the appetite-suppressing peptide POMC in a hypothalamic cell line in vitro, which indicates that biglycan acts on the appetite regulatory central system to treat obesity through appetite suppression (FIGS. 1 and 2).

In another embodiment of the present invention, as a result of administering biglycan in an amount of 1 mg per kg of body weight to an animal model with obesity induced by a high-fat diet, it was found that weight gain was reduced (FIG. 3, graphs A and B), and the biglycan-administered group exhibited a remarkably lower food consumption rate than the high-fat diet group (FIG. 3, graphs C and D). In addition, there was a difference in total fat weight between the biglycan-administered group and the high-fat diet group as a control group (FIG. 3, graph E), and the average weight of the quadriceps in the biglycan-administered group was much higher than that in the high-fat diet group (FIG. 3, graph F).

Therefore, in the present invention, biglycan regulates diet-related pathways by inhibiting the expression of appetite-promoting peptides and promoting the expression of appetite-suppressing peptides. This indicates that biglycan has therapeutic efficacy for obesity by reducing food intake and body weight through appetite suppression and thus can be used as a pharmaceutical composition for suppressing appetite or treating obesity.

The pharmaceutical composition of the present invention may further contain an appropriate carrier, excipient, or diluent commonly used in the preparation of pharmaceutical compositions.

The pharmaceutical composition according to the present invention may be administered orally or parenterally, and the parenteral administration may be selected from external application to the skin, intraperitoneal injection, intrarectal injection, subcutaneous injection, intravenous injection, intramuscular injection, or intrathoracic injection, but is not limited thereto.

The pharmaceutical composition according to the present invention may be formulated and used as an oral formulation such as a powder, granule, tablet, capsule, suspension, emulsion, syrup, or aerosol, or an external preparation, suppository or sterile injectable solution. Examples of the carrier, excipient, or diluent that may be contained in the pharmaceutical composition according to the present invention may comprise lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. Upon preparation of a formulation, typically used diluents or excipients, such as fillers, extenders, binders, wetting agents, disintegrants, or surfactants, are used. Solid formulations for oral administration may comprise, but are not limited to, tablets, pills, powders, granules, capsules and the like, and these solid formulations may be prepared by mixing a mixed herbal pharmaceutical ingredient with at least one excipient, for example, starch, calcium carbonate, sucrose, lactose, gelatin, or the like. In addition to simple excipients, lubricants such as magnesium stearate and talc are also used. Liquid formulations for oral administration may be suspensions, oral liquids and solutions, emulsions, syrups and the like, and may include various excipients such as wetting agents, sweeteners, fragrances, preservatives and the like, in addition to water and liquid paraffin, which are simple diluents that are commonly used.

Formulations for parenteral administration may comprise sterilized aqueous solutions, non-aqueous solvents, suspensions, emulsions, lyophilizates and suppositories. Examples of such non-aqueous solvents and suspensions comprise propylene glycol, polyethylene glycol, vegetable oil such as olive oil, injectable esters such as ethyl oleate, and the like. The basic substance of a suppository may comprise Witepsol, macrogol, Tween 61, cacao butter, laurin butter, glycerogelatin and the like.

The preferred dosage (administered amount) of the pharmaceutical composition according to the present invention may vary depending on the condition and weight of the patient, severity of disease, and the form, route, and duration of administration of the drug, and may be determined by those skilled in the art in consideration of these factors. For example, the pharmaceutical composition of the present invention may be administered in a daily dose of 0.00001 to 1 g/kg, more preferably 0.0001 to 500 mg/kg, to provide the desired effects. The composition of the present invention may be administered once a day, or may be administered several times after being divided into multiple doses. The dosage of the composition does not limit the scope of the present invention in any aspect.

The pharmaceutical composition of the present invention may be administered as a single therapeutic agent or in combination with other therapeutic agents, and may be administered sequentially or simultaneously with a conventional therapeutic agent. In addition, the pharmaceutical composition may be administered in single or multiple doses. Taking into consideration these factors, it is important to administer the minimum amount sufficient to achieve maximum efficacy without side effects.

In another aspect, the present invention is directed to a method for preventing or treating obesity comprising administering biglycan to a subject.

In another aspect, the present invention is directed to a method for suppressing appetite comprising administering biglycan to a subject.

In another aspect, the present invention is directed to the use of biglycan for the prevention or treatment of obesity.

In another aspect, the present invention is directed to the use of biglycan for suppression of appetite.

In another aspect, the present invention is directed to the use of biglycan for the preparation of a medicine for preventing or treating obesity.

In another aspect, the present invention is directed to the use of biglycan for the preparation of a medicine for suppressing appetite.

As used herein, the term "subject" refers to any animal, including a human, that suffers from or is at risk of obesity, and the disease can be effectively prevented or treated by administering the composition according to the present invention thereto.

In another aspect, the present invention is directed to a functional food for preventing or alleviating obesity containing biglycan as an active ingredient.

As used herein, the term "amelioration" refers to any action that at least reduces the severity of the parameters associated with the condition to be treated, e.g. the degree of symptoms.

In another aspect, the present invention is directed to a method for preventing or treating obesity comprising administering biglycan to a subject.

In another aspect, the present invention is directed to the use of biglycan for the prevention or treatment of obesity.

In another aspect, the present invention is directed to the use of biglycan for the preparation of a medicine for treating or preventing obesity.

In the present invention, the biglycan may be represented by the amino acid sequence of SEQ ID NO: 1.

In the present invention, the biglycan preferably inhibits the expression of an appetite-stimulating peptide, and the appetite-stimulating peptide is preferably agouti-related protein (AgRP) or neuropeptide Y (NPY), but is not limited thereto.

In the present invention, the biglycan preferably enhances the expression of an appetite-suppressing peptide, and the appetite-suppressing peptide is preferably proopiomelanocortin (POMC), but is not limited thereto.

In addition, the biglycan preferably reduces food intake, and more preferably reduces food intake by suppressing appetite.

When the food composition of the present invention is used as a food additive, the food composition may be used alone or in combination with other food or food additives, and can be suitably used in accordance with a conventional method. In general, when preparing food or a beverage, the composition of the present invention is added in an amount of 15% by weight or less, preferably 10% by weight or less, based on the total amount of raw material. However, in the case of long-term intake for the purpose of health and hygiene or for the purpose of health regulation, the amount may be within the range defined above, and it will be obvious that the active ingredient may be used in an amount exceeding the above range because there is no problem with regard to safety.

The food of the present invention may be prepared in any form, such as that of a functional food, nutritional supplement, health food, or food additive. For example, the composition of the present invention as a health food may be prepared in the form of a tea, juice or drink for drinking, or may be granulated, encapsulated, and powdered for ingestion. In addition, functional foods may be prepared by adding the composition of the present invention to beverages (including alcoholic beverages), fruits and processed foods thereof (e.g., canned fruit, bottled food, jam, marmalade, etc.), fish, meat and processed foods thereof (e.g., ham, sausage, corned beef, etc.), bread and noodles (e.g. udong, soba, ramen, spaghetti, macaroni, etc.), fruit juice, various drinks, cookies, Yeot (Korean hard taffy), dairy products (e.g. butter, cheese, etc.), edible vegetable oils, margarine, vegetable protein, food contained in a retort pouch, frozen food, various seasonings (e.g., miso, soy sauce, other sauces, etc.), and the like.

The health functional food includes, as a food composition, various forms such as functional foods, nutritional supplements, health foods, food additives, etc., and the health functional food may be provided by preparing the composition of the present invention in any of various forms, such as teas, juices or drinks, or performing granulation, encapsulation, or powderization, or by adding these compounds or extracts to various foods such as beverages, fruits and processed foods, fish, meat and processed foods, breads, noodles, seasonings and the like according to conventional methods known in the art.

The health beverage composition may contain additional ingredients such as various flavors or natural carbohydrates, like general beverages. The natural carbohydrates include monosaccharides such as glucose and fructose, disaccharides such as maltose and sucrose, and natural sweeteners such as dextrin and cyclodextrin. In addition, synthetic sweeteners such as saccharin and aspartame may be used. The proportion of the natural carbohydrate may be appropriately selected by those skilled in the art.

In addition to the ingredients described above, the composition of the present invention may contain various nutrients, vitamins, electrolytes, flavors, colorants, pectic acid and salts thereof, alginic acid and salts thereof, organic acids, protective colloidal thickeners, pH adjusters, stabilizers, preservatives, glycerin, alcohols, carbonating agents used in carbonated beverages, and the like. In addition, the composition of the present invention may contain pulp for the production of natural fruit juices, fruit juice beverages and vegetable beverages. These components may be used alone or in combination. The proportion of these additives can also be appropriately selected by those skilled in the art.

Hereinafter, the present invention will be described in more detail with reference to examples. However, it will be obvious to those skilled in the art that these examples are provided only for illustration of the present invention and should not be construed as limiting the scope of the present invention.

Example 1: Confirmation of Suppression of Appetite-Stimulating Peptide Expression by Biglycan In Vitro N41, hypothalamus cells expressing appetite-stimulating peptides, namely agouti-related protein (AgRP) and neuropeptide Y (NPY) (Imperatore et al., *Pharmacol. Res.* 111: 600-609, 2016; Oh et al., *Autophagy* 12:2009-2025, 2016; Sasaki et al., *Endocrinology* 151:2556-2566, 2010, (Cellutions Biosystems Inc., CLU121)) were cultured in DMEM containing 10% FBS and 1% penicillin-streptomycin at 37° C. in an atmosphere of 5% $CO_2$. Then, the cells were each treated with 0 ng/ml, 10 ng/ml, and 100 ng/ml of biglycan, and cultured for 1 hour, 12 hours and 24 hours. The control used herein was cells treated with the solution used to dissolve biglycan (0.1% BSA). Then, mRNA expression was measured using real-time PCR.

As shown in FIG. 1, the result showed that treatment with biglycan remarkably decreased expression of mRNA of the appetite-stimulating peptides AgRP and NPY compared to the case in which treatment with biglycan was not performed (FIG. 1).

Example 2: Confirmation of Enhancement of Appetite-Suppressing Peptide Expression by Biglycan In Vitro N43/5, hypothalamic cells expressing the appetite-suppressing peptide, proopiomelanocortin (POMC) (Cai et al., *J. Endocrinol.* 192:605-614, 2007; Cakir et al., *The Journal of Biological Chemistry* 288:17675-17688, 2013; Oh et al., *Autophagy* 12:2009-2025, 2016, (Cellutions Biosystems Inc, CLU121)) were cultured in DMEM containing 10% FBS and 1% penicillin-streptomycin at 37° C. in an atmosphere of 5% $CO_2$. Then, the cells were respectively treated with 0 ng/ml, 10 ng/ml and 100 ng/ml of biglycan, and cultured for 1 hour, 12 hours and 24 hours. The control used herein was cells treated with the solution used to dissolve biglycan (0.1% BSA). Then, mRNA expression was measured using real-time PCR.

As shown in FIG. 2, the result showed that treatment with biglycan remarkably increased expression of mRNA of the appetite-suppressing peptide, POMC, compared to the case of non-treatment with biglycan (FIG. 2).

Example 3: Confirmation of Appetite Suppression and Weight Gain Suppression Effects by Biglycan in Obesity-Induced Animal Model An obesity-induced animal model was produced, and the effect of biglycan on suppressing appetite and weight gain was determined using the model.

First, 9 mice (C57BL/6J male) were fed a high-fat diet (HFD) for 4 weeks to produce an obesity-induced animal model.

A biglycan-administered group was produced by administering biglycan into the abdominal cavity of each mouse at a dose of 1 mg/kg body weight once every two days.

4 weeks after obesity induction, the difference in weight gain was determined between the high-fat-diet (HFD) group and the biglycan-administered high-fat-diet group (BGN) (administered with biglycan in a dose of 1 mg/Kg body weight) (FIG. 3, graph A). The final body weight of the biglycan-administered group (BGN) was remarkably lower than that of the high-fat diet group (HFD) (FIG. 3, graph B).

In addition, the biglycan-administered group exhibited a remarkably lower food consumption rate than the high-fat diet group (FIG. 3, graphs C and D).

There was a difference in total fat weight, calculated as the sum of epididymal fat and subcutaneous fat between the high-fat diet group and the biglycan-administered group (FIG. 3, graph E). Interestingly, the average weight of the quadriceps muscles of the biglycan-administered group was much higher than that of the high-fat diet group (FIG. 3, graph F).

INDUSTRIAL APPLICABILITY

The biglycan according to the present invention induces appetite suppression by inhibiting the expression of the appetite-stimulating peptides Agrp and NPY and promoting the expression of the appetite-suppressing peptide, POMC, and thus is very useful as a therapeutic agent for obesity.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Listing Free Text]
An electronic file is attached.

---

The invention claimed is:

1. A method of suppressing appetite of a human subject in need thereof, comprising administering to said human subject a pharmaceutical composition in an administration form of a powder, granule, tablet, capsule, suspension, emulsion, syrup, aerosol, parenteral composition, or suppository, said pharmaceutical composition containing biglycan comprising the sequence of SEQ ID NO: 1 in an effective appetite suppressing amount.

2. The method according to claim 1, wherein the biglycan is administered to said human subject at a dose in a range of from 0.0001 to 500 mg/kg.

* * * * *

UNITED STATES PATENT AND TRADEMARK OFFICE
CERTIFICATE OF CORRECTION

| | | |
|---|---|---|
| PATENT NO. | : 12,048,731 B2 | Page 1 of 1 |
| APPLICATION NO. | : 17/602750 | |
| DATED | : July 30, 2024 | |
| INVENTOR(S) | : Hyeon Soo Kim et al. | |

It is certified that error appears in the above-identified patent and that said Letters Patent is hereby corrected as shown below:

In the Claims

Column 12, Line 34, "SEO ID NO: 1" should be -- SEQ ID NO: 1 --.

Signed and Sealed this
Fifteenth Day of October, 2024

Katherine Kelly Vidal
*Director of the United States Patent and Trademark Office*